(12) United States Patent
Levin et al.

(10) Patent No.: US 11,696,732 B2
(45) Date of Patent: Jul. 11, 2023

(54) SYSTEM AND METHOD FOR SUBJECT SHAPE ESTIMATION

(71) Applicant: General Electric Company, Schenectady, NY (US)

(72) Inventors: Ilan Levin, Alone Abba (IL); Yaron Hefetz, Kibbutz Alonim (IL); Avi Bar-Shalev, Haifa (IL); Avishai Ofan, Rehovot (IL)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1091 days.

(21) Appl. No.: 16/222,419

(22) Filed: Dec. 17, 2018

(65) Prior Publication Data

US 2019/0117173 A1    Apr. 25, 2019

Related U.S. Application Data

(63) Continuation of application No. 14/278,091, filed on May 15, 2014, now Pat. No. 10,188,358.

(51) Int. Cl.
| | | |
|---|---|---|
| A61B 6/04 | (2006.01) | |
| A61B 5/107 | (2006.01) | |
| A61B 5/00 | (2006.01) | |
| A61B 6/00 | (2006.01) | |
| A61B 6/03 | (2006.01) | |

(Continued)

(52) U.S. Cl.
CPC ............. *A61B 6/04* (2013.01); *A61B 5/0037* (2013.01); *A61B 5/0077* (2013.01); *A61B 5/1079* (2013.01); *A61B 6/037* (2013.01); *A61B 6/0407* (2013.01); *A61B 6/4258* (2013.01); *A61B 6/4417* (2013.01); *A61B 6/461* (2013.01); *A61B 6/488* (2013.01); *A61B 6/544* (2013.01); *A61B 6/58* (2013.01); *G01T 1/1644* (2013.01); *A61B 6/0487* (2020.08); *A61B 6/4266* (2013.01); *A61B 6/503* (2013.01); *A61B 6/5205* (2013.01); *A61B 6/545* (2013.01); *A61B 6/547* (2013.01); *A61B 6/588* (2013.01); *A61B 8/08* (2013.01); *G06T 11/005* (2013.01)

(58) Field of Classification Search
CPC ....... A61B 6/04; A61B 5/0037; A61B 5/0077; A61B 5/1079; A61B 6/037; A61B 6/0407; A61B 6/4258; A61B 6/4417; A61B 6/461; A61B 6/488; A61B 6/544; A61B 6/58; A61B 6/0487; A61B 6/4266; A61B 6/503; A61B 6/5205; A61B 6/545; A61B 6/547; A61B 6/588; A61B 8/08; G01T 1/1644; G06T 11/005
See application file for complete search history.

(56) References Cited

U.S. PATENT DOCUMENTS

| | | |
|---|---|---|
| 5,381,791 A | 1/1995 | Qian |
| 7,103,144 B2 | 9/2006 | Wong et al. |

(Continued)

*Primary Examiner* — Joseph M Santos Rodriguez
*Assistant Examiner* — Kaitlyn E Sebastian
(74) *Attorney, Agent, or Firm* — The Small Patent Law Group LLC; Dean D. Small

(57) ABSTRACT

A medical imaging system is provided. Imaging detector columns are installed in a gantry to receive imaging information about a subject. Imaging detector columns can extend and retract radially as well as be rotated orbitally around the gantry. The system can automatically adjust setup configuration and an imaging operation based on subject shape estimation information.

14 Claims, 11 Drawing Sheets

(51) Int. Cl.
  *G01T 1/164* (2006.01)
  *G06T 11/00* (2006.01)
  *A61B 8/08* (2006.01)

(56) References Cited

U.S. PATENT DOCUMENTS

| | | |
|---|---|---|
| 8,582,720 B2 | 11/2013 | Morton |
| 9,029,791 B1 | 5/2015 | Kovalski et al. |
| 2006/0002511 A1* | 1/2006 | Miller ................... A61N 5/1049 378/65 |
| 2006/0091315 A1* | 5/2006 | Hawman ................. A61B 6/037 250/363.04 |
| 2007/0194222 A1* | 8/2007 | Takayama ............. G01T 1/1663 250/252.1 |
| 2008/0029704 A1 | 2/2008 | Hefetz et al. |
| 2011/0026685 A1 | 2/2011 | Zilbertsein et al. |
| 2011/0237941 A1 | 9/2011 | Shahar et al. |
| 2012/0002780 A1* | 1/2012 | Forthmann ............. G16H 50/30 382/128 |
| 2013/0032715 A1* | 2/2013 | Zhu ......................... A61B 6/483 378/147 |
| 2013/0123602 A1* | 5/2013 | Kovalski ............... A61B 6/0407 600/407 |
| 2013/0248719 A1* | 9/2013 | Volokh ................... A61B 6/037 250/362 |
| 2013/0294570 A1* | 11/2013 | Hansis ................. A61B 6/5294 378/4 |
| 2013/0294671 A1* | 11/2013 | Iida ....................... G06T 11/003 382/131 |
| 2013/0317326 A1 | 11/2013 | Balberg et al. |
| 2014/0086382 A1 | 3/2014 | Flohr et al. |

* cited by examiner

SYSTEM AND METHOD FOR SUBJECT SHAPE ESTIMATION

RELATED APPLICATIONS

The present application is a continuation of, and claims priority to, U.S. patent application Ser. No. 14/278,091, filed May 15, 2014, entitled, "Systems and Methods for Subject Shape Estimation," the subject matter of which is hereby incorporated in its entirety.

BACKGROUND

The subject matter disclosed herein relates generally to medical imaging systems, and more particularly subject shape estimation for imaging operations.

Medical imaging systems are used to assist with diagnosis of medical ailments in patients. Such systems include Nuclear Medicine (NM) imaging systems which can be Single Photon Emission Computed Tomography (SPECT) imaging systems or Positron Emission Tomography (PET) imaging systems. A goal of these systems is to provide high quality images of a subject to an operator, while keeping exposure to any radioactivity, otherwise known as dose, to a minimum.

One way to achieve a higher quality image is to position image detector units close to a subject of the image scan. To do so safely and without contact with the subject requires determining a surface profile of a subject under inspection that is positioned at a distance from image detector units. Previously, this subject shape, or surface profile, estimation may have been done with a Computed Tomography (CT) apparatus included in the medical imaging system. But a CT apparatus adds expense to the purchaser of the medical imaging system and could add unnecessary dose to the subject of the scan. Thus, what is needed is a non-contact and non-CT system of estimating subject shape for improved medical imaging operations.

BRIEF DESCRIPTION

In accordance with an embodiment, an adaptive imaging system is taught, comprising: a gantry; a plurality of imaging detector units installed in the gantry, at least one of the plurality of detector units movable relative to the gantry to position at least one of the detector units with respect to a subject; a controller for controlling the independent position of at least one detector unit; and wherein the controller adaptively alters at least one detector unit position for an imaging operation based on subject shape estimation information. The adaptive alteration can comprise determining the current location of at least one detector unit; estimating the outer shape of the subject; calculating a placement location near the subject of at least one detector unit based on said subject information; and controlling the movement of the at least one detector unit to said placement location. The system can further comprise an image reconstruction module; and a display; wherein the system acquires image information from the detector units, reconstructs the data into a three-dimensional image, and outputs the three-dimensional image on the display.

In alternate embodiments, the system estimates the outer shape of a subject in the system. In an embodiment, the system can comprise: a plurality of light emitting sources attached to the gantry; a plurality of light detectors attached to the gantry; and wherein estimating the outer shape of the subject comprises successively emitting light from at least two light emitting sources and detecting which light detectors received each instance of emitted light. The gantry has a bore; the plurality of light emitting sources are attached around the ring of the bore; and the plurality of light detectors are attached around the ring of the bore in line with the plurality of light emitting sources. In an embodiment, the system can comprise: a plurality of ultrasonic range finders attached to the gantry; wherein estimating the outer shape of the subject comprises the range finders issuing ultrasonic pulses towards the subject and receiving ultrasonic echoes. In an embodiment, the system can comprise: the subject comprises an isotope that emits radioactivity; and estimating the outer shape of the subject comprises receiving direct radioactive emission information and scatter radioactive emission information to at least one of the detector units. Further, the direct radioactive emission information may be used for both estimating the outer shape of the subject and medical image generation; and the scatter radioactive emission information may be used solely for estimating the outer shape of the subject. In an embodiment, the system can comprise: an optical camera that generates three-dimensional images of a portion of a subject; and wherein estimating the outer shape of the subject comprises utilization of shape information from said three-dimensional images.

In accordance with an embodiment, the system uses no x-rays for subject shape estimation. In accordance with an embodiment, detector units/columns can be moved into multiple radial positions.

In accordance with an embodiment, a non-transitory computer readable storage medium is taught, having stored thereon a computer program comprising instructions, which, when executed by a computer, cause the computer to: determine a subject shape estimation of a subject of a medical imaging system with a gantry, wherein the gantry does not include an x-ray tube; develop an image acquisition scenario with the subject shape estimation and a requested imaging operation; configure a physical location of a least one detector unit attached to the gantry based on the developed image acquisition scenario; and acquire Single Photon Emission Computed Tomography (SPECT) image information from the detector units.

In accordance with an embodiment, an imaging method is taught, comprising: determining, at multiple time instances, exterior shape estimation of a subject of a medical imaging system with a gantry, wherein the gantry does not include an x-ray tube; creating a summary shape estimation by combining the outermost shape of the exterior shape estimation of at least two time instances; altering a physical location of a plurality of detector units attached to the gantry based on the summary shape estimation; and acquiring Single Photon Emission Computed Tomography (SPECT) image information from the plurality of detector units.

DETAILED DESCRIPTION

Figure 1:
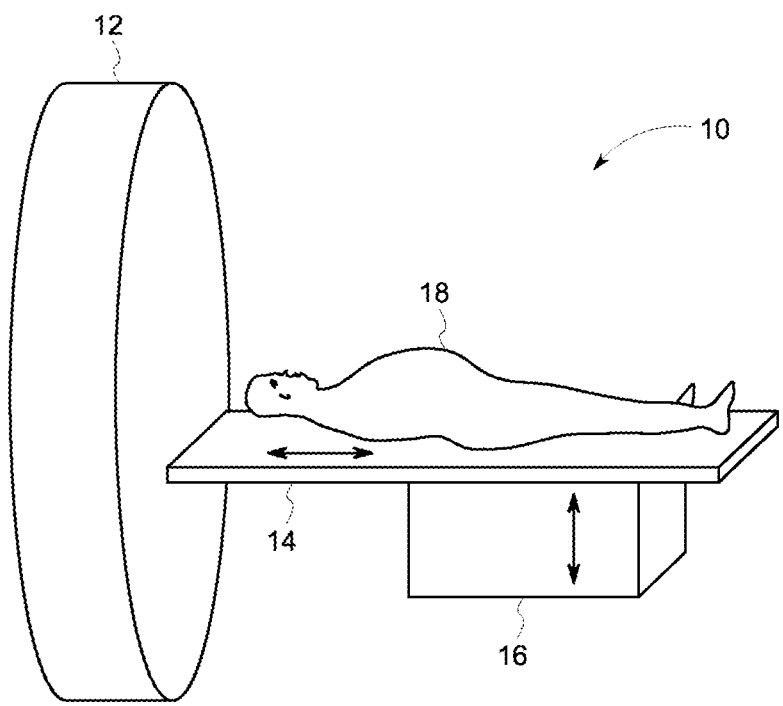
FIG. 1 shows a medical imaging system, in accordance with an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a medical imaging system, and in particular, a Nuclear Medicine (NM) imaging system having a gantry with a plurality of different types of imaging detectors mounted thereto. For example, in various embodiments of an NM imaging system, a Single Photon Emission Computed Tomography (SPECT) imaging scanner is provided that includes a plurality of detectors with a single type of detectors, or a combination of different types of detectors, that acquire SPECT image information. The various embodiments may include detectors formed from different materials, having different configurations or arrangements, having different collimation, etc. The system may be configured to perform single isotope or multi-isotope imaging.

It should be noted that although the various embodiments are described in connection with a particular NM imaging system, such as a SPECT detector system, the various embodiments may be implemented in connection with other imaging systems, such as a Positron Emission Tomography (PET) imaging system.

The system and method provide object shape determination at fast speeds. The external shape profile of an object is determined without using harmful x-rays and without touching the object. The object can be a subject, or patient, of a medical imaging system. Quickly knowing the shape of the object to be scanned allows an imaging system to configure its image detection devices and other system components for best image capture. This can include image detectors, gantry rotation, table position, and other system components. Some image processing may be done to ensure that the external shape profile, or outline, is indeed correct.

FIG. 1 shows a medical imaging system 10 in accordance with an embodiment. A subject 18 can be a human patient in one embodiment. It should be noted that the subject 18 does not have to be human. It can be some other living creature or inanimate object in various embodiments. The subject 18 can be placed on a pallet 14 that can move a subject horizontally for locating the subject in the most advantageous imaging position. The bed mechanism 16 can raise and lower the pallet 14 vertically for locating the subject in the most advantageous imaging position. The gantry 12 is shown as circular in one embodiment. In other embodiments the gantry 12 may be of any shape such as square, oval, "C" shape, or hexagonal.

Figure 2:
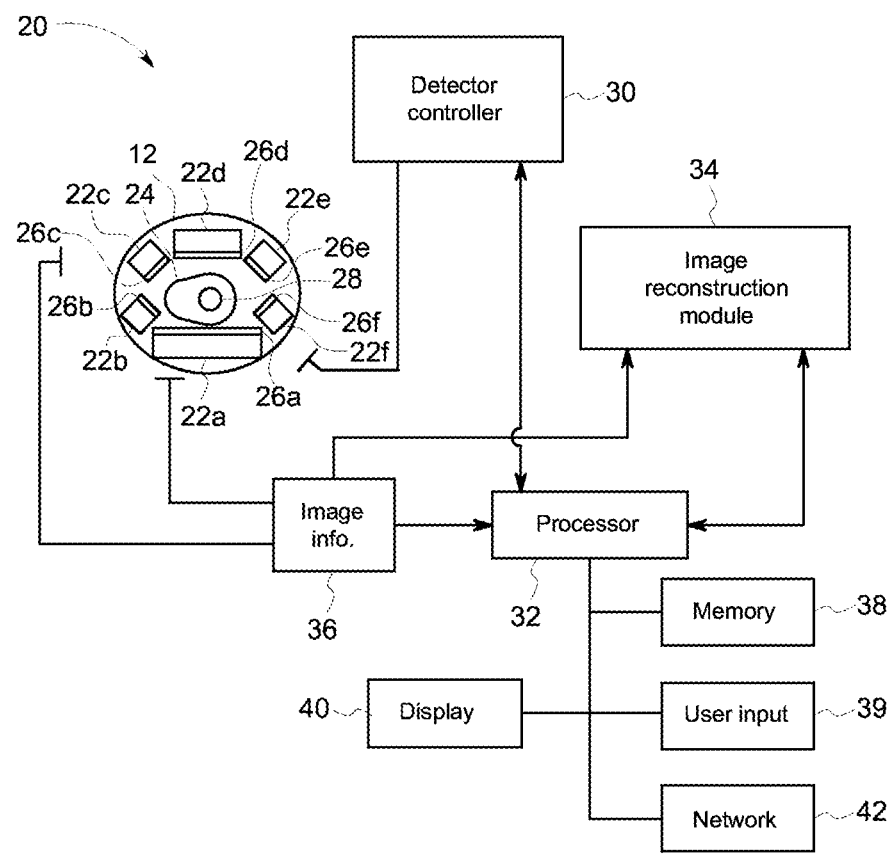
FIG. 2 shows a block diagram of a medical imaging system, in accordance with an embodiment.

FIG. 2 shows a block diagram of medical imaging system 20 in accordance with an embodiment. The medical imaging system 20 may be provided having a plurality of NM cameras configured as SPECT detector columns 22a-22f. It should be noted that the various embodiments are not limited to the medical imaging system 20 having six detector columns 22 as shown or to the sizes or shapes of the illustrated detector columns 22. For example, the medical imaging system 20 may include more or less detector columns 22 having different shapes and/or sizes, or formed from different materials. The medical imaging system 20 in various embodiments is configured as a hybrid SPECT system having a plurality of detector columns 22, wherein at least two of the detectors are formed from different materials, have different configurations or arrangements, have different collimation, or are otherwise different.

In operation, a subject, such as a patient 24, is positioned in proximity to the one or more of the detector columns 22 for imaging. The imaging system 20 can then re-adjust the detector columns 22 further from or closer to the patient 24 or imaging area of interest as needed, which is heart 28 in an example embodiment. Imaging of patient 24 is performed by one or more of the detector columns 22. The imaging by each of the detector columns 22 may be performed simultaneously, concurrently, or sequentially.

The position of the detector columns 22 may be varied, including the relative position between detector columns 22, tilt, angle, swivel, etc. of the detector columns 22. Additionally, each of the detector columns 22 may have a corresponding collimator 26a-26f mounted or coupled thereto. The collimators 26a-26f likewise may be of different types. One or more detector columns 22 may be coupled to a different type of collimator 26 (e.g., parallel hole, pin-hole, fan-beam, cone-beam, etc.). Accordingly, in various embodiments, the detector column 22 wholly includes collimator 26.

The detector columns 22 may include single crystal, or multi-crystal, detectors or pixelated detectors or scintillator based detectors that are configured to acquire SPECT image data. For example, the detector columns 22 may have detector elements formed from different materials, such as semiconductor materials, including Cadmium Zinc Telluride (CdZnTe), often referred to as CZT, Cadmium Telluride (CdTe), and Silicon (Si), among others, or non-semiconductor scintillator materials such as different types of crystal scintillators, for example, Sodium Iodide (NaI), Bismuth Germanate (BGO), Cerium-doped Lutetium Yttrium Orthosilicate (LYSO), Gadolinium Oxyorthosilicate (GSO), Cesium Iodide (CsI), Lanthanum (III) bromide ($LaBr_3$), among others. Additionally suitable components may be provided. For example, the detector columns 22 may be coupled to photosensors, such as an array of Photo-Multiplier Tubes (PMTs), an Avalanche Photodiode Detector (AFD), etc.

The imaging system 20 can also include a detector controller 30 that operates to control the movement of the detector columns 22 and/or the collimators 26. For example, the detector controller 30 may control movement of the detector columns 22, such as to rotate or orbit the detector columns 22 around a patient 24, and which may also include moving the detectors closer or farther from the patient 24 and pivoting/swiveling the detector columns 22, such that more localized movements or motions are provided. In an exemplary embodiment, a detector unit within column 22 pivots about an axis substantially parallel to the length of patient 18 such that collimator 26 associated with the detector unit within column 22 views patient 18 from several orientations. The detector controller 30 additionally may control the orbital rotation of the detector columns 22 around the edges of the gantry bore, such that the detector columns 22 are at a new angle to the patient 24 than previously. The detector controller 30 may also optionally control movement of the collimators 26, such as independently of the detector columns 22. It should be noted that one or more the detector columns 22 and/or the collimators 26 may move during imaging operation, move prior to, but remain stationary during imaging operation, or may remain in a fixed positioned or orientation. In various embodiments, the detector controller 30 may be a single unit controlling movement of both the detector columns 22 and the collimators 26, may be separate units, or may be a single unit controlling only operation of the detector columns 22 or may be a single unit controlling only operation of the collimators 26.

The imaging system 20 also includes an image reconstruction module 34 configured to generate images from acquired image information 36 received from the detector columns 22. For example, the image reconstruction module 34 may operate using NM image reconstruction techniques to generate SPECT images of the patient 24, which may include an object of interest, such as the heart 28. The image reconstruction techniques may be determined based on the installation status of detector column 22 acquiring the image information 36 and sending to image reconstruction module 34 and/or processor 32.

Variations and modifications to the various embodiments are contemplated. For example, in a multi-headed system, namely a system having two or more detector columns 22, each detector column 22 may be formed from different materials and have different collimators 26. Accordingly, in at least one embodiment, one detector combination may be configured to obtain information for an entire field of view (FOV), such as the entire spine, while another detector combination is configured to focus on a smaller region of interest (ROI) to provide higher quality information (e.g., more accurate photon counting). Additionally, information acquired by one detector combination may be used to adjust the position, orientation, etc. of at least one other detector combination during imaging.

The image reconstruction module 34 may be implemented in connection with or on a detector controller 30 and/or processor 32 that is coupled to the imaging system 20. Optionally, the image reconstruction module 34 may be implemented as a module or device that is coupled to or installed in the detector controller 30 and/or processor 32. Each processing module may be a separate hardware module or software module, or combined together into one chip or module in various embodiments.

The image information 36 received by the processor 32 and/or image reconstruction module 34 may be stored for a short term (e.g., during processing) or for a long term (e.g., for later offline retrieval) in a memory 38. The memory 38 may be any type of data storage device, which may also store databases of information. The memory 38 may be separate from or form part of the processor 32. A user input 39, which may include a user interface selection device, such as a computer mouse, trackball and/or keyboard is also provided to receive a user input. User input 39 may direct the processor 32 to send a detector control signal to the detector controller 30 for alteration of the detector column 22 arrangement in the gantry bore. Optionally, user input 39 may be considered by the processor 32 as a suggestion and the processor 32 may choose to not execute the suggestion based on criteria.

Thus, during operation, the output from the detector columns 22, which may include the image information 36, such as projection data from a plurality of detector/gantry angles is transmitted to the processor 32 and the image reconstruction module 34 for reconstruction and formation of one or more images. The images can be three-dimensional (3D). The reconstructed images and other user output can be transmitted to a display 40 such as a computer monitor or printer output. The reconstructed images and other user output can also be transmitted to a remote computing device via network 42.

Different combinations and variations of detector columns 22 and/or collimators 26 will now be described. It should be noted that the various embodiments are not limited to a particular detector, collimator, or detector combination, but may include any imaging system having a plurality of different types of detector columns 22 and/or collimators 26, for example, having at least two detector columns 22 of a different type or design. Additionally, the number of detector columns 22 and the arrangement thereof may be varied as desired or needed, for example, based on the type of imaging to be performed or the type of image information to be acquired. Accordingly, various embodiments include the imaging system 20 having a plurality of detector columns 22, wherein at least two of the detector columns 22 are different and are configured to perform imaging of the patient 24 (or other object).

It should be noted that as used herein, a set of detectors is generally referred to as the detector columns 22 and a set of collimators is generally referred to as the collimators 26. Moreover, the use of letter designations after the numeral designation for the detector columns 22 and collimators 26 are used for ease of illustration and do not necessarily represent the same detector columns 22 or collimators 26 in the various embodiments or figures. Thus, the letter designation represents the relative positioning of the detector columns 22 or collimators 26 and not necessarily the type or kind of detector. Additionally, the size and shape of the detector columns 22 may be varied as desired or needed.

Figure 3:
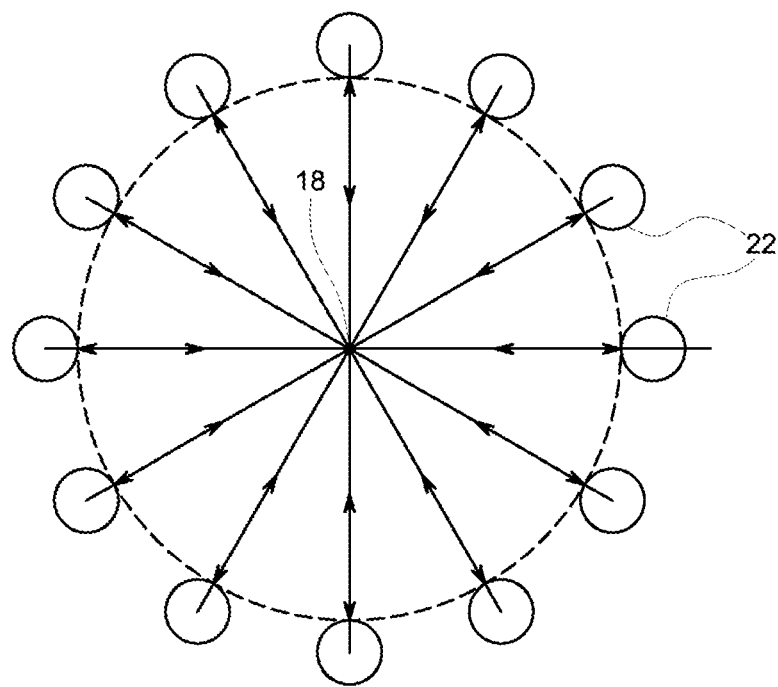
FIG. 3 shows a radial construction of an imaging system, in accordance with an embodiment.

FIG. 3 shows a radial construction of an imaging system in accordance with an embodiment. Twelve detector columns 22 are placed at a consistent angle, thirty degrees in this example, from each other along the inside of a gantry bore. Thus, the detector columns 22 are uniformly distributed in this example. Each detector column 22 is movable along a radial axis. This allows the detector columns 22 to be closer or further from a subject 18 for imaging. The circles in the FIG. depict the location of a detector head of detector column 22. The detector columns are shown along the dotted line as their outer limit position in this view of one embodiment. The dual head radial arrows depict the in-out direction of motion of the detector columns 22.

Figure 4:
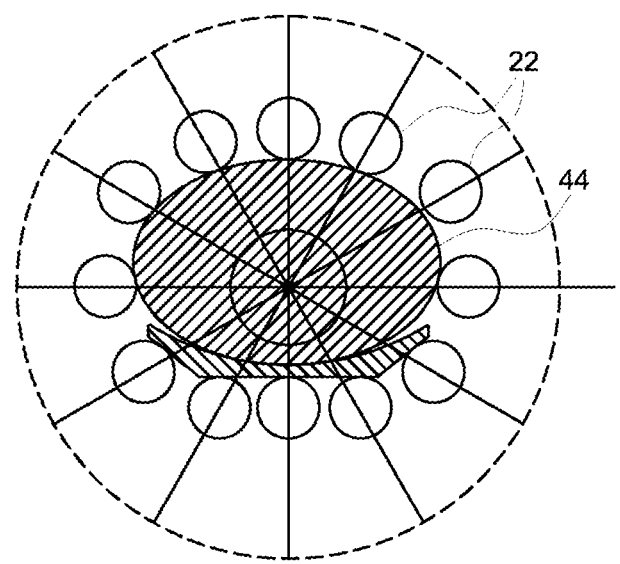
FIG. 4 shows a radial construction of an in-use imaging system, in accordance with an embodiment.

FIG. 4 shows a radial construction of an in-use imaging system, where twelve detector columns 22 have their heads placed at a consistent angle and have been moved radially inward to be in positions close to a surface profile 44 of a subject. As FIG. 4 shows, some of the detector heads are further towards the center of their radial axis than others. This allows for high-quality imaging results with varied-sized objects. Each detector column 22 may also include a proximity sensor for determining if the detector column will collide with any object while it moves. Determination of the best axial location of each detector column and detector head is discussed herein below.

Figure 5:
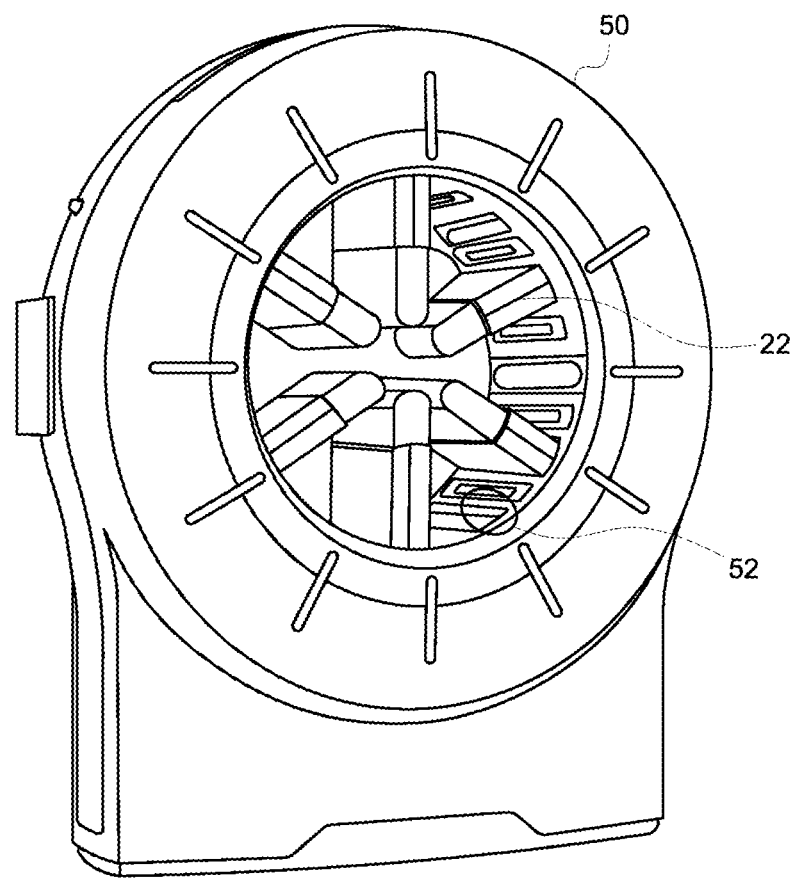
FIG. 5 shows a partially populated medical imaging system, in accordance with an embodiment.

FIG. 5 shows a partially populated medical imaging system, in accordance with an embodiment. Gantry 50 can support twelve detector columns 22. Gantry 50 can contain all of the features of the FIG. 2 system in one embodiment. Only six detector columns 22 have been installed in gantry 50. This could be for lower cost of the system, easier maintenance, or other reasons, for example. Thus, the system of FIG. 5 is a partially populated NM imaging system. Compared to a fully populated system, such as FIG. 3 and FIG. 4, a partially populated system includes the installation of a partial amount of detector columns 22 that an imaging system is configured to support. It is partially populated because installation information for the system indicates that the system can support twelve detector columns 22, but only six detector columns 22 are installed. The locations where a detector column can be installed or attached can be called receiver locations 52 in some embodiments. The detector columns 22 in FIG. 5 are shown in a radially extended position.

Figure 6:
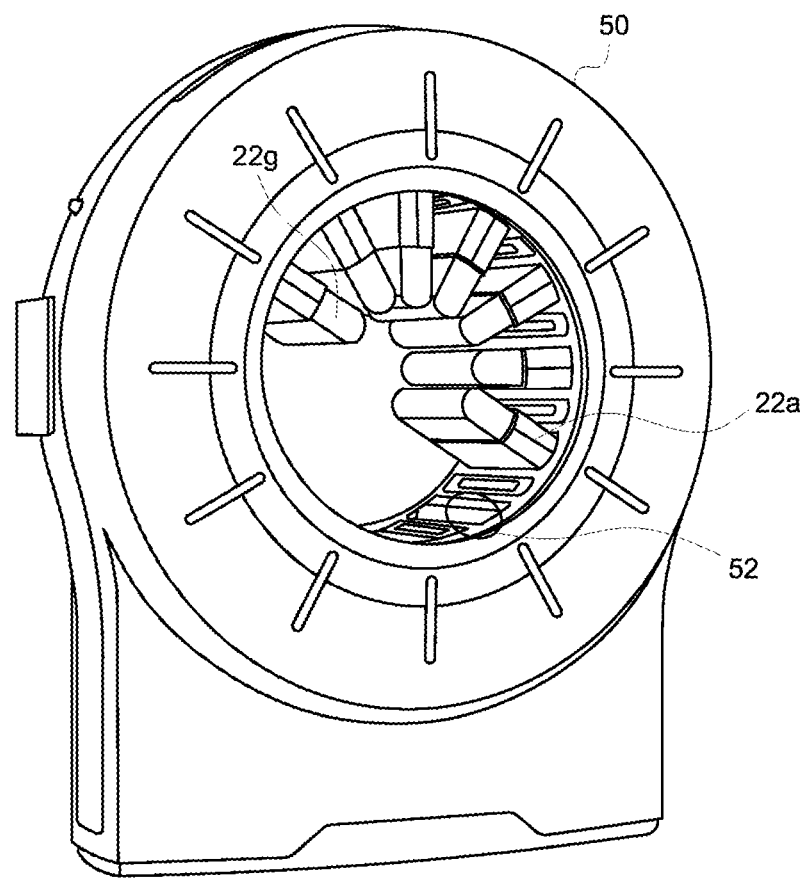
FIG. 6 shows a gantry that can support the installation and operation of a plurality of detector columns, in accordance with an embodiment.

FIG. 6 shows a gantry 50 that can support the installation and operation of twelve detector columns 22, in accordance with an embodiment. Only seven detector columns 22a-22g have been installed in gantry 50. This is an example of a partially populated imaging system. Detector columns 22 in FIG. 6 are shown in a radially extended manner, but not as radially extended as shown in FIG. 5. This may be because of the shape of the patient. This configuration may be best for a supine patient where the heart, as an example of a ROI, is near the top and side of the gantry. The detector controller 30 can identify that there are seven installed detector columns 22 and in which receiver locations 52 they reside around the bore of gantry 50. Then the detector controller 30 rotates the detector columns 22 around the bore to the ideal position for the particular region of interest based on user input 39, patient shape information, or information of the test and patient from other sources, such as memory 38 or network 42. This ideal position can also be called the position location essential for imaging information. Thus, moving the detector columns 22 into the best position for capturing essential imaging information for each type of procedure is important and is done by various embodiments.

Figure 7:
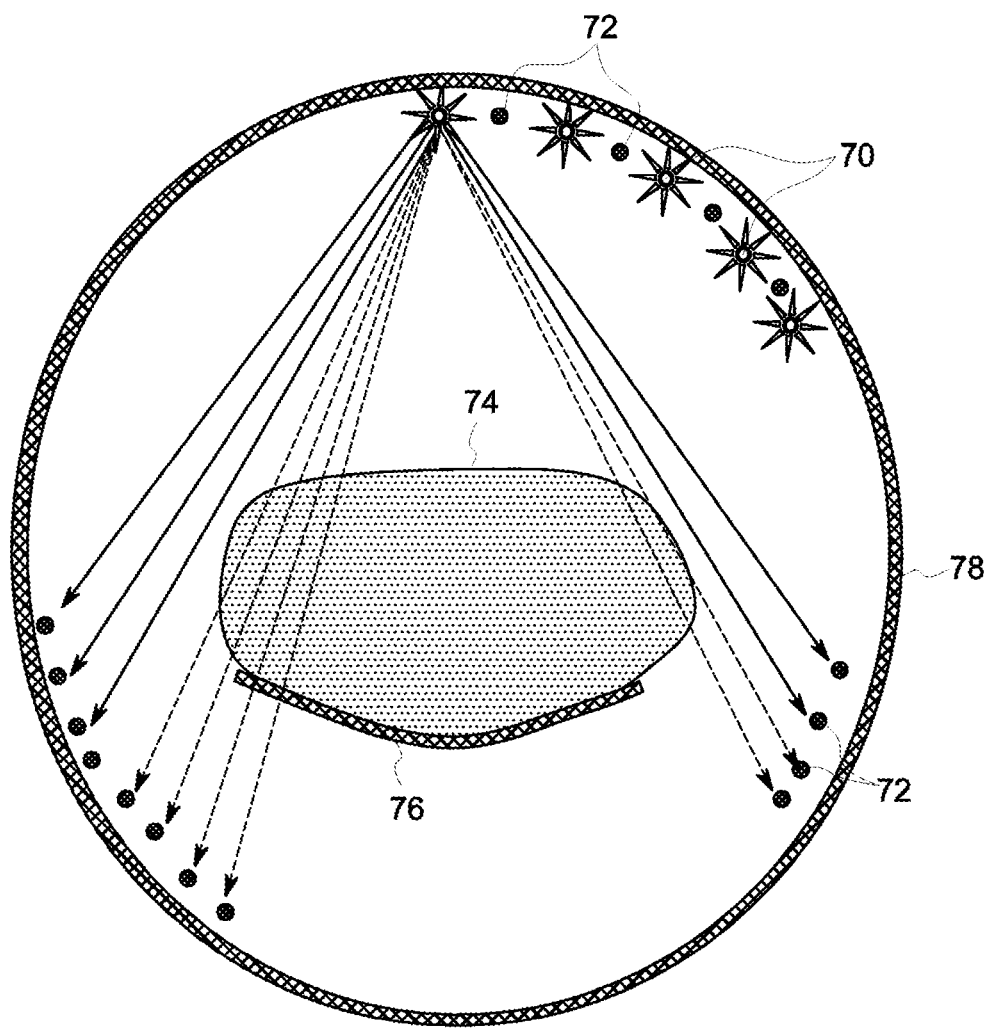
FIG. 7 shows a light-based shape estimation system, in accordance with an embodiment.

FIG. 7 shows a light-based shape estimation system, in accordance with an embodiment. Subject 74 rests on table 76 for an imaging operation. Prior to moving image detector columns into place for the imaging operation, the system performs a subject shape estimation. This allows the image detector columns to be close to, but not touching, the subject, for best image quality. Such a setup is shown in FIG. 4.

In order to estimate subject shape, gantry 78 has installed light emitting sources 70 and light detectors 72. Light emitting sources 70 can be light emitting diodes (LED) in an embodiment. Light detectors 72 can be photo-diodes in an embodiment. Light emitting sources 70 and light detectors 72 are installed around the ring of gantry 78. FIG. 7 shows a partial, exemplary layout, but many useful layouts are contemplated. Light emitting sources 70 and light detectors 72 can be placed all the way around the ring. They can be placed as pairs near each other, or there can be double or triple the total amount of light detectors 72 around the ring compared to light emitting sources 70. This may depend also on the specific technology chosen to emit and detect the light. In addition, the light emitting sources 70 and light detectors 72 can be placed towards the front or back of the gantry for a full ring, or be placed in the center of the gantry between where the arms would extend. Thus, for example, there could be twelve light emitting sources and either twelve or twenty-four light detectors around the gantry of FIG. 3, placed in between detector columns 22. In another configuration, for example, three light emitting sources 70 may be installed between two nearby light detectors 72.

In an exemplary operation, individual light emitting sources 70 emit light at different times. This may be done in an ordered sequence according to an embodiment. The light emitted from any particular light emitting source 70 will only arrive at some of the light detectors 72, as shown in FIG. 7. The solid lines indicate that emitted light has hit a light detector 72. The dotted lines indicate that emitted light has not hit a light detector 72 because the light was obscured by the subject. Thus at a particular system time instance, the system knows which light emitting source 70 emitted the light and which light detectors 72 received the emitted light. The system processor 32, or a separate processing unit in the gantry, then can estimate a subject shape using contour information across multiple time instances. The subject shape at one axial position of the table is now determined and, if so desired, the table 76 can be moved in the axial direction to have the system continue to estimate the shape of additional sections of a subject.

Figure 8:
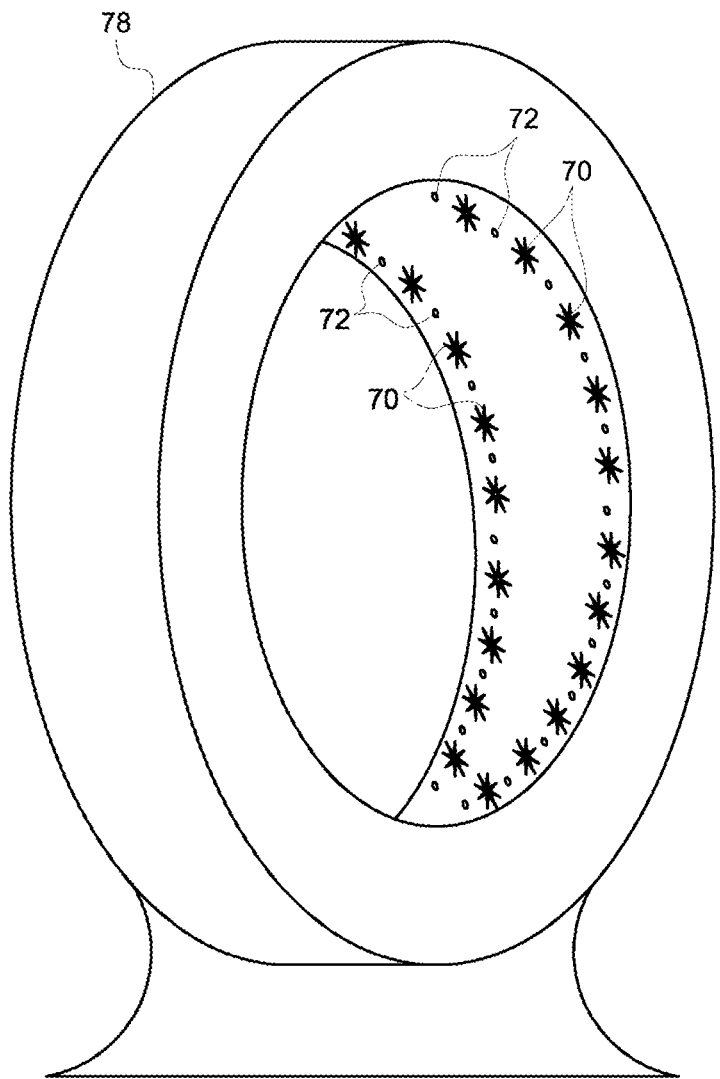
FIG. 8 shows a light-based shape determination system with dual rings of lights, in accordance with an embodiment.

FIG. 8 shows a light-based shape determination system with dual rings of lights, in accordance with an embodiment. Light emitting sources 70 and light detectors 72 are shown in pairs. The pairs can be placed fully around the gantry bore. The pairs can be axially on either side of any installed detector columns. A dual-ring system as shown in FIG. 8 can speed up the subject shape estimation process.

In addition to assisting in positioning the detectors close to the patient, knowing the patient shape may be used to prevent collision of the detector columns with parts of the patient as the patient is moved into the bore of the gantry for imaging. Placing the optical transceivers (sources and detectors) near the edge of the gantry, for example outwards from the edge of the detector columns may be used to detect approaching increase of patient shape such as shoulders as the patient is moved on the table with his head towards the gantry and retract the detector columns (which are presumably positioned close to the patient's head) before they collide with the shoulders. Having two rings of optical transceivers enables to scan the patient without collisions while the table moves in one direction or the other. Although patient's shape that was measured while the patient was moved into the bore may be stored and used when the patient is moved back, a second ring of transceivers at the other edge may be used to ensure that the patient did not move or changed his position (such as lifting an arm or folding his knees) since the last measurement of body shape. It should be noted that in most cases detector columns are retracted before the patient is moved out of the patient bore, and thus collision is unlikely at this stage. However, back and forth motion may need to be executed by the table for dynamic imaging of an organ (or organs) larger than the axial length of the FOV (Field Of View) of the camera. In these cases, having two rings may be advantageous as columns need not be retracted and imaging may be performed on both table motion directions. For greater accuracy, the sparsity of the light sources and detectors may be compensated by small rotation or dithering of the gantry.

Figure 9:
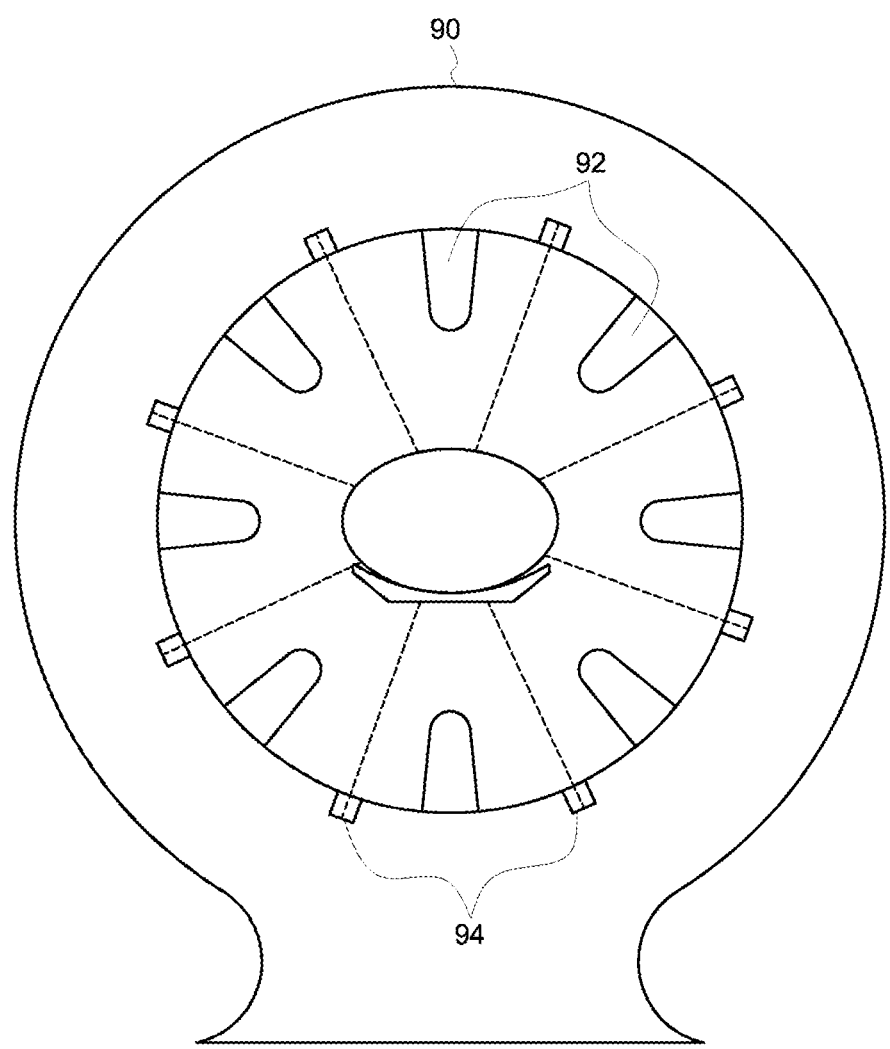
FIG. 9 shows a front view of a medical imaging system with range finders that assist with subject shape estimation, in accordance with an embodiment.

FIG. 9 shows a front view of a medical imaging system with range finders that assist with subject shape estimation, in accordance with an embodiment. Gantry 90 of a medical imaging system includes detector columns 92 for detecting emissions from a subject to form a medical image. Between detector columns 92, range finders 94 are installed in gantry 90 to help estimate subject shape. While eight range finders 94 are shown, additional configurations are contemplated. Detector columns 92 are best set to a retracted state during a subject shape estimation process.

Range finders 94 can be ultrasonic transducers in one embodiment. A range finder 94 can emit short pulse of sound and interpret the timing of sound wave echoes to determine the distance to a subject. Having range finders 94 placed around the bore of gantry 90 allows for subject distance information from many angles that can be combined by a computer processing unit into subject shape estimation information. Range finders 94 can be optical transducers in another embodiment. For example laser rangefinders may be used. A laser range finder can emit short pulse of light, or a train of short light pulses, and interpret the timing of reflected light to determine the distance to a subject. For greater accuracy, the sparsity of the range finders may be compensated by small rotation or dithering of the gantry. Each stream of light pulses can be encoded, so each laser rangefinder can be identified as unique. This prevents interfering communications.

Figure 10:
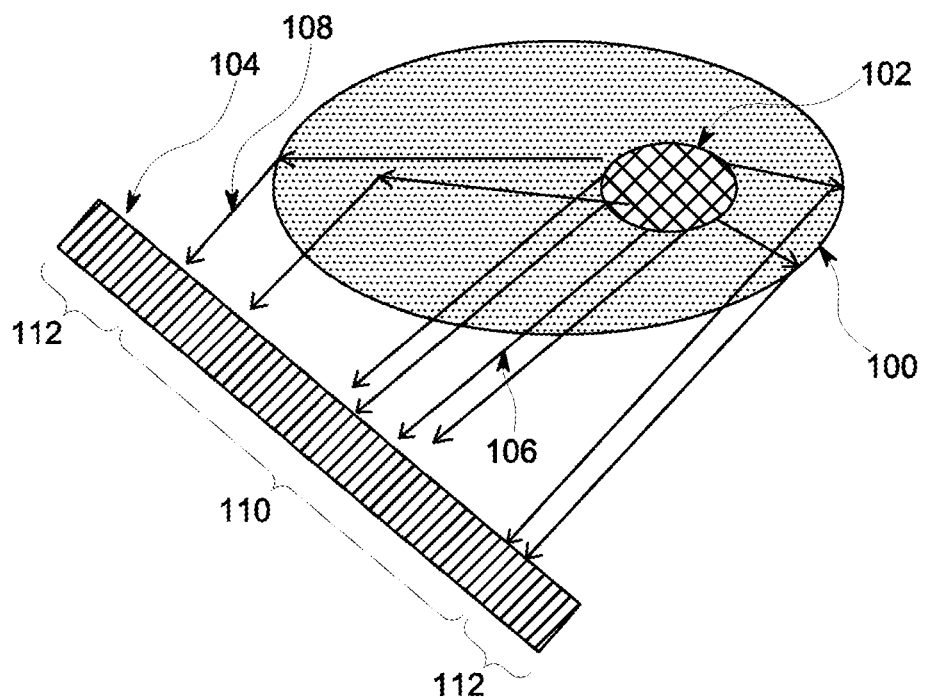
FIG. 10 shows an imaging system that collects scattered radiation to estimate subject shape, in accordance with an embodiment

FIG. 10 shows an imaging system that collects scattered radiation, or emissions, to estimate subject shape, in accordance with an embodiment. Subject 100 is placed in the imaging system with a radioactive isotope already injected as needed for nuclear imaging. For demonstration purposes, the radioactive isotope is shown as a single radiation source 102. Detector system 104 is designed to detect instances of radiation. Detector system 104 may be the combination of a detector column 22 and detector collimator 26, as shown in FIG. 2.

Direct radiation 106 passes through the patient in a straight line and hits the detector system 104. In conventional nuclear imaging, only the direct radiation 106 is used to reconstruct the image and thus parts of the patient's body having no (or very little) concentration of radioactivity are not seen in the image. In addition, scattered radiation 108 hits the detector system 104. FIG. 10 shows four instances of scattered radiation hitting detector system 104. Scattered radiation occurs as radiation starts traveling in one direction in a subject and is deflected towards the detector system 104 as the result of inelastic interaction with electrons in the patient's tissue. Scattered radiation may follow the principles of Compton scattering and the scattered radiation is at energies below the original energy peak of the radioactive isotope. In conventional nuclear imaging, an energy window at the detection system rejects such scattered detected photons. For the purpose of finding the patient shape, energy windowing at the detection system is increased to accept the scattered radiation. Thus, in the direction that detector system 104 is angled towards the patient, detection footprint 110 can be detected. No photons are detected in non-incident areas 112. The detection footprint 110 information from multiple detector systems 104 placed at different angles, such as shown in FIG. 2, can be combined to quickly estimate the shape of a subject. The system of FIG. 10 would not require additional hardware to be added to the system and can be considered low-cost.

It should be noted that due to the negligible scattering properties of air, volume outside the patient would not emit, nor scatter any radiation. Preferably, a binary image is reconstructed, for example by placing a low threshold to the number of counts in an image pixel (or reconstructed image voxel) that above which the pixel (voxel) is assumed to be within the patient's perimeter. Optionally, smoothing or other image processing may be applied to the reconstructed patient's perimeter of reconstructed image.

In an exemplary embodiment, a preliminary imaging of the patient is performed while the columns are at least partially retracted (column below the table may be placed near the table without fear of collision as the location and shape of the table is known to the system). The preliminary image includes the scattered radiation and the reconstructed image may be used for determining the patient's shape. Optionally, direct and scattered radiation is concurrently gathered, but kept in separate datasets. The combined scattered and direct radiation is used for determining the patient's shape, while the direct radiation is used for conventional SPECT imaging. It should be noted that while a preliminary may have a degraded resolution, it nevertheless may reveal the location of the targeted organ (for example the heart in cardiac imaging) via the direct radiation, as well as the non-targeted tissue (for example the rest of the torso) via the scattered radiation. It should be noted that non-target tissue intervene with imaging the target organ(s) by both preventing placement of the detection units near the target organ, and by attenuating the radiation emitted from it. By analyzing both target and intervening non-target tissue, imaging strategy may be determined and optionally optimized. Such imaging strategy may include at least some of: positioning the columns; determining the range of pivoting of the detector units; determining optimal height of the table (to enable optimal placement of the columns); determining optimal rotation angle of the gantry (to enable optimal placement of the columns); setting imaging duration (by estimating the time needed to acquire clinically satisfying image taking into account the distance from detectors to the target organ, the radiation from the target-organ, and the attenuation).

Figure 11:
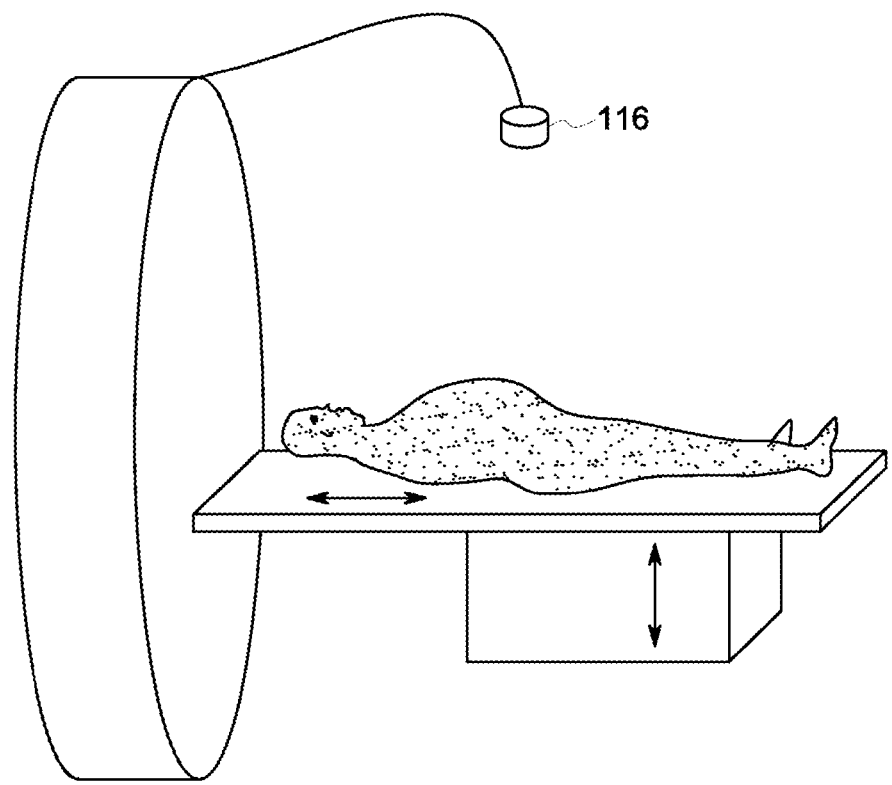
FIG. 11 shows a side view of a medical imaging system including a camera for estimating subject shape, in accordance with an embodiment.

FIG. 11 shows a side view of a medical imaging system including a camera for estimating subject shape, in accordance with an embodiment. Camera 116 can be connected to the gantry system in a variety of ways; FIG. 11 shows just one example attachment. Camera 116 can be a three-dimensional (3D) optical camera and may have one or a plurality of lenses. Camera 116 can include an infrared light emitter in an embodiment. Camera 116 can quickly detect the shape of the subject through 3D detection technologies. These may include, for example, computing a depth map of the subject by analyzing a speckle pattern of infrared laser light, and then inferring body position. In a system with multiple lenses, a stereoscopic image may be taken to achieve three-dimensional information. Camera 116 can generate 3D images of a portion of the subject. The portion may be the full subject or a partial section of the subject. Camera 116 can also be used for subject identification, via face recognition for example, and matching with a patient health record, in accordance with an embodiment.

The three-dimensional estimation of the subject body shape can be for portions of a subject or the whole body. Thus, at any axial location of the table inside the gantry, the system can have the estimated shape for that portion of the subject's body.

Figure 12:
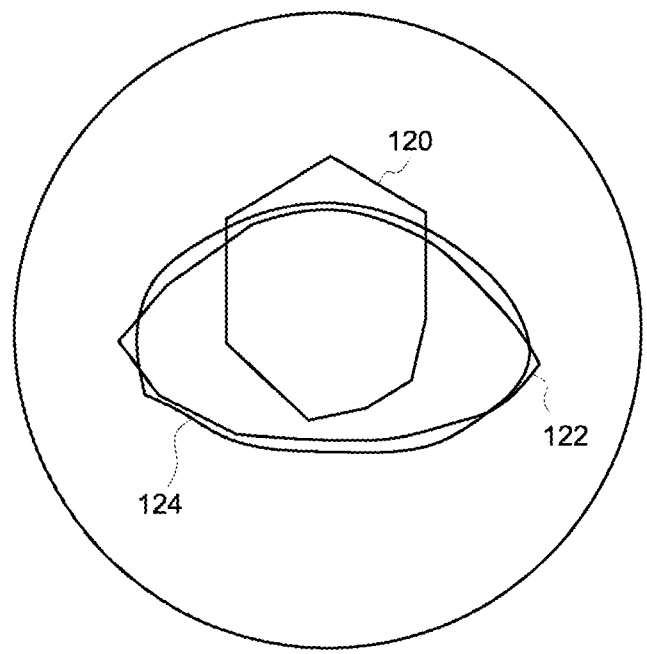
FIG. 12 shows a digital view of multiple shape estimations, in accordance with an embodiment.

FIG. 12 shows a digital view of multiple shape estimations, in accordance with an embodiment. Each T time, the curvature is calculated. All the curvatures of the subject found between the entrance and the exit of the bore are stored. A first shape estimation 120 is estimated based on information at a first time. A second shape estimation 122 is estimated based on information at a second time. And a third shape estimation 124 is estimated based on information at a third time. For example, this could be three separate times as a subject is moved through a gantry bore in the axial direction. This is done by a movable gantry table, an example of which is shown in FIG. 1. The system may also have multiple times at one axial position of the table in order to capture the maximum subject shape at that axial position. This is due to the fact that as the subject breathes, their shape can shift slightly. This could be, for example, the difference in shape between 122 and 124. Alternatively, the difference in shape between 122 and 124 is based on the axial position of the table with respect to the gantry.

Figure 13:
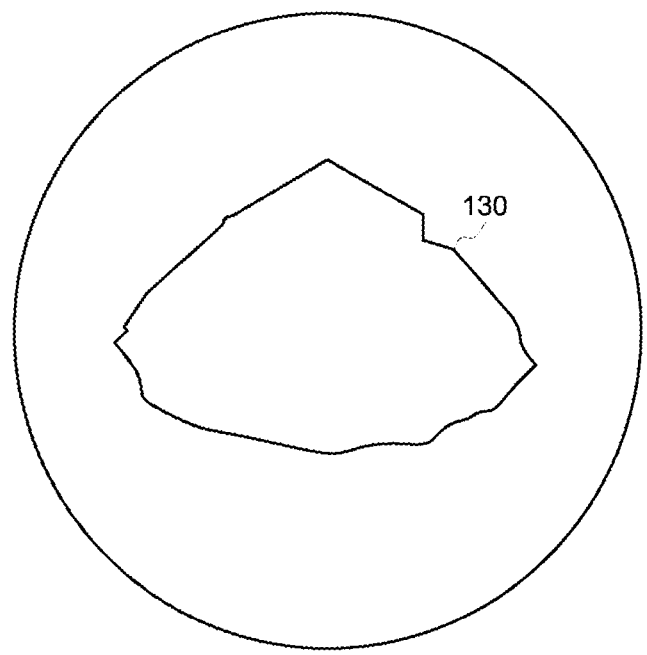
FIG. 13 shows a digital view of a unified shape estimation, in accordance with an embodiment.

FIG. 13 shows a digital view of a unified shape estimation, in accordance with an embodiment. The unified shape estimation 130 is calculated by the system based on the maximum extent of any single subject shape estimation. Described another way, unified shape estimation 130 is a union of the most expansive parts of any single subject shape estimation. For example, the top of unified shape estimation 130 takes its shape from first shape estimation 120, while the right tip of unified shape estimation 130 takes its shape from second shape estimation 122. This allows the system to have a single, unified subject shape estimation.

Figure 14:
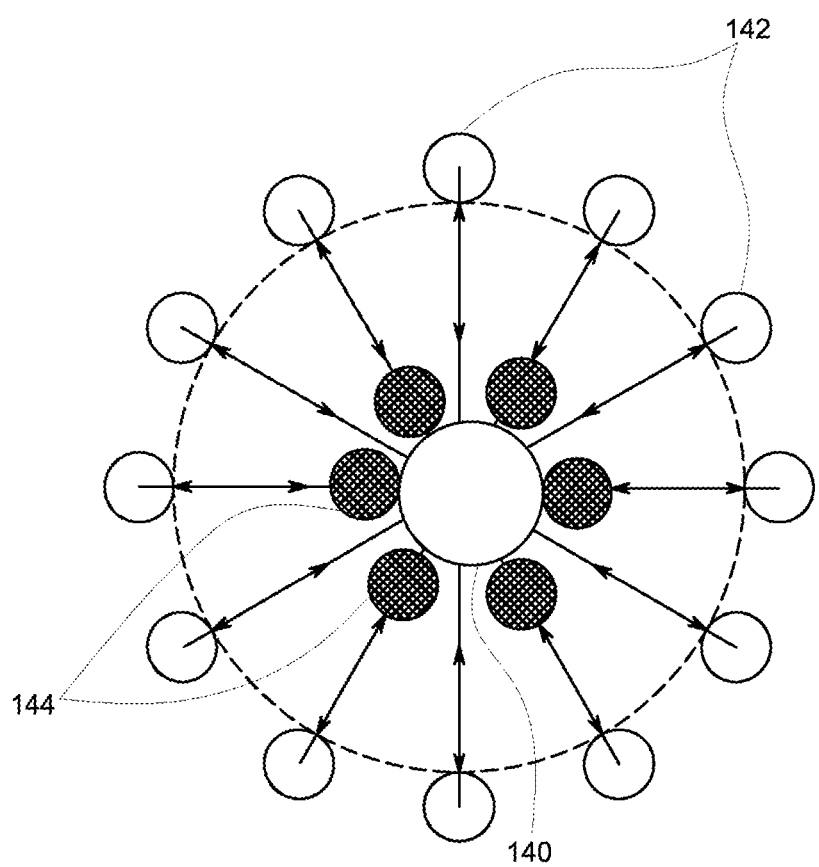
FIG. 14 shows a front view of a medical imaging system utilizing unified shape estimation information, in accordance with an embodiment.

FIG. 14 shows a front view of a medical imaging system utilizing unified shape estimation information, in accordance with an embodiment. Unified shape estimation 140 has been calculated. Using unified shape estimation 140, the system has determined that only six of the twelve detector columns are needed for this scan. Thus, retracted detector columns 142 have been deemed as unneeded for the current operation. Extended detector columns 144 have been set into place for a medical imaging operation. In addition, extended detector columns 144 can be set relatively close to the subject for best image quality because the system knows the shape of the subject.

If the scan required the detectors to be rotated around the patient, unified shape estimation 140 would also help determine when to retract and extend certain detector columns based on the upcoming shape the detector column may encounter. This prevents any collision with the subject or table.

The system can use unified shape estimation 140 to determine which detector columns to use in a situation where some detector columns extend further than others, are of different shapes and sizes, or when some detector column receiver slots do not have a column installed in one or more locations around the gantry.

The configurable and controllable system of some embodiments could be controlled by user input. Thus, the user can override the automatic operation of the system and take full specific control of components of the system through a user interface.

The systems and methods contemplated herein provide for rapid ways to estimate the shape of a subject for a medical imaging procedure. These ways of estimation are low or no dose, providing better subject safety. These ways of estimation do not require a CT scanner (including an x-ray tube) in the system, saving on cost and reducing x-ray radiation to a subject. The estimated shape can then be used for optimal detector column and table placement for the medical imaging procedure. This automatic shape estimation and adjustment of the system can save setup time compared with a human operator completing the same steps. With optimal detector column and table placement, a higher quality image can be obtained and a physician can have better medical information for decision-making.

Body external shape information may be used to the estimate the location of the targeted organ or organs (for example the heart in cardiac imaging) via the use of patient atlas. By analyzing a typical matching patient from an atlas of SPECT imaged patients, imaging strategy may be determined and optionally optimized. Such imaging strategy may include at least some of: positioning the columns; determining the range of pivoting of the detector units; determining optimal height of the table (to enable optimal placement of the columns); determining optimal rotation angle of the gantry (to enable optimal placement of the columns); setting imaging duration (by estimating the time needed to acquire clinically satisfying image taking into account the distance from detectors to the target organ, the radiation from the target-organ, and the attenuation). Optionally, an interpolation or morphing of one or several atlas images may be used for generation of a model of the patient that matches the patient shape.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a flash memory disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A detector system comprising:
   a nuclear medicine imaging detector; and
   at least one processor operably coupled to the nuclear medicine imaging detector, the at least one processor configured to:
      operate the nuclear medicine imaging detector to perform a preliminary imaging with the nuclear medicine imaging detector at least partially retracted,
      identify direct radiation acquired with the nuclear medicine imaging detector using a first energy window for the preliminary imaging,
      identify scattered radiation acquired with the nuclear medicine imaging detector using a second energy window for the preliminary imaging,
      determine a patient border using at least the scattered radiation for the preliminary imaging; and
      operate the nuclear medicine imaging detector to perform a subsequent imaging with the nuclear medicine imaging detector extended more closely to the patient than during the preliminary imaging, wherein the nuclear medicine imaging detector is positioned to perform the subsequent imaging based on the determined patient border.

2. The detector system of claim 1, wherein the patient border is determined based on a detection footprint defined by identified scattered radiation.

3. The detector system of claim 1, wherein the second energy window includes lower energies than the first energy window.

4. The detector system of claim 1, wherein the at least one processor is configured to concurrently acquire the direct radiation and scattered radiation, and store the direct radiation and scattered radiation in different datasets.

5. The detector system of claim 1, wherein the at least one processor is configured to determine the patient border using the scattered radiation and the direct radiation.

6. The detector system of claim 1, wherein the nuclear medicine imaging detector is mounted to a gantry and movable relative to the gantry to position the imaging detector with respect to a subject.

7. A method comprising:
   performing a preliminary imaging with a nuclear medicine imaging detector with the nuclear medicine imaging detector at least partially retracted;
   acquiring radiation including both direct radiation and scattered radiation from an object with the nuclear medicine imaging detector for the preliminary imaging;
   identifying the direct radiation acquired with the nuclear medicine imaging detector using a first energy window for the preliminary imaging,
   identifying the scattered radiation acquired with the nuclear medicine imaging detector using a second energy window for the preliminary imaging,
   determining a patient border using at least the scattered radiation for the preliminary imaging; and
   operating the nuclear medicine imaging detector to perform a subsequent imaging with the nuclear medicine imaging detector extended more closely to the patient than during the preliminary imaging, wherein the nuclear medicine imaging detector is positioned to perform the subsequent imaging based on the determined patient border.

8. The method of claim 7, wherein the second energy window includes lower energies than the first energy window.

9. The method of claim 7, wherein the direct radiation and scattered radiation are concurrently acquired, the method further comprising storing the direct radiation and scattered radiation in different datasets.

10. The method of claim 7, wherein the patient border is determined using the scattered radiation and the direct radiation.

11. A non-transitory computer readable storage medium having stored thereon a computer program comprising instructions, which, when executed by a computer, cause the computer to:

perform a preliminary imaging with a nuclear medicine imaging detector with the nuclear medicine imaging detector at least partially retracted, acquire radiation including both direct radiation and scattered radiation from an object with the nuclear medicine imaging detector for the preliminary imaging, identify the direct radiation acquired with the nuclear medicine imaging detector using a first energy window for the preliminary imaging, identify the scattered radiation acquired with the nuclear medicine imaging detector using a second energy window for the preliminary imaging, determine a patient border using at least the scattered radiation for the preliminary imaging; and operate the nuclear medicine imaging detector to perform a subsequent imaging with the nuclear medicine imaging detector extended more closely to the patient than during the preliminary imaging, wherein the nuclear medicine imaging detector is positioned to perform the subsequent imaging based on the determined patient border.

12. The computer readable storage medium of claim 11, wherein the second energy window includes lower energies than the first energy window.

13. The computer readable storage medium of claim 11, wherein the direct radiation and scattered radiation are concurrently acquired, wherein the instructions cause the computer to store the direct radiation and scattered radiation in different datasets.

14. The computer readable storage medium of claim 11, wherein the patient border is determined using the scattered radiation and the direct radiation.

* * * * *